United States Patent [19]

Peter

[11] Patent Number: 4,940,811
[45] Date of Patent: Jul. 10, 1990

[54] N,N-DISUBSTITUTED UREAS AND PROCESSES FOR THEIR MANUFACTURE

[75] Inventor: Heinrich Peter, Binningen, Switzerland

[73] Assignee: Ciba-Geigy Corporation, Ardsley, N.Y.

[21] Appl. No.: 126,981

[22] Filed: Nov. 30, 1987

[30] Foreign Application Priority Data

Dec. 9, 1986 [CH] Switzerland .......................... 4907/86
Jul. 23, 1987 [CH] Switzerland .......................... 2793/87

[51] Int. Cl.$^5$ .......................................... C07C 175/06
[52] U.S. Cl. ....................................... 558/262; 560/25; 560/29; 560/34; 560/158; 560/159
[58] Field of Search .............. 558/262; 560/158, 159, 560/25, 34, 29

[56] References Cited

U.S. PATENT DOCUMENTS

3,634,407 1/1972 Gaumann .......................... 260/239.3
4,671,901 6/1987 Green .............................. 260/404.5

FOREIGN PATENT DOCUMENTS

1163337 2/1964 Fed. Rep. of Germany .
WO85/03290 8/1985 PCT Int'l Appl. .
WO86/03745 7/1986 PCT Int'l Appl. .
WO86/03747 7/1986 PCT Int'l Appl. .

OTHER PUBLICATIONS

Chem. Abstr., 100: 185755z (1984).
H. Bickel et al., Helv. Chem. Acta XLVI, pp. 1385-1389 (1963).

*Primary Examiner*—Paul J. Killos
*Attorney, Agent, or Firm*—JoAnn Villamizar

[57] ABSTRACT

N,O-acylates, derived from N-acylated carbamic acids, of desferrioxamine B of the formula

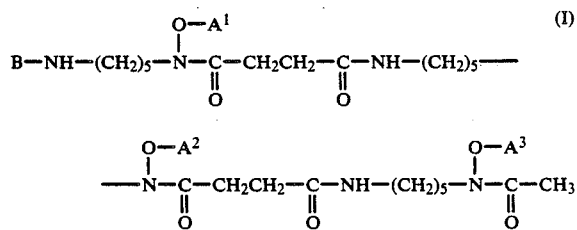

(I)

in which B represents a carbamoyl radical of the partial formula —CO—NH—Alk—CO—O—$R_a^1$ (II) in which $R_a^1$ represents $C_1$–$C_4$-alkyl or $C_2$–$C_4$-alkyenyl and Alk represents $C_1$–$C_7$-alkylene that is optionally substituted by hydroxy, $C_1$–$C_4$-alkanoyloxy, amino, $C_1$–$C_4$-alkoxycarbonyl, carbamoyl, phenyl, hydroxyphenyl, methoxyphenyl or by indolyl, and each of the symbols $A^1$, $A^2$ and $A^3$, independently of the others, represents hydrogen, an acyl radical Ac derived from a carboxylic acid, or an above-defined carbamoyl radical of the partial formula II, form strong iron(III) and aluminium complexes in living cells. They can therefore be used therapeutically for the treatment of pathological conditions in warm-blooded animals, including humans, that are associated with an excess of iron(III) or aluminium in the body or are caused by iron(III)-dependent pathogenic organisms. The compounds according to the invention can be obtained, for example, by conventional reaction of desferrioxamine B, or a suitable N- and O-silylated derivative thereof, with an isocyanatoalkanoic acid ester.

29 Claims, No Drawings

N,N-DISUBSTITUTED UREAS AND PROCESSES FOR THEIR MANUFACTURE

The invention relates to novel N,N'-disubstituted ureas, derived from hydroxamic acids, especially from trihydroxamic acids, which are known by the name ferrioxamines and specifically desferrioxamines as metabolites of microorganisms, especially actinomycetes. Of these, the invention relates especially to the N,N'-disubstituted ureas derived from desferrioxamine B, and the O-acylates thereof, of the general formula I

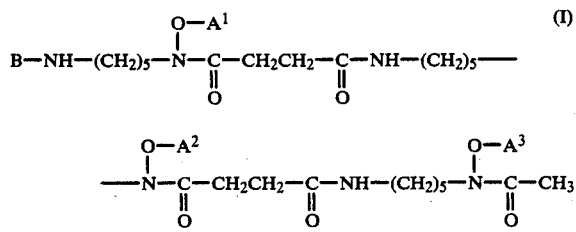

in which B represents a carbamoyl radical of the partial formula $-CO-NH-Alk-CO-O-R_a{}^1$ (II) in which $R_a{}^1$ represents $C_1$-$C_4$-alkyl or $C_2$-$C_4$-alkenyl and Alk represents $C_1$-$C_7$-alkylene that is unsubstituted or substituted by hydroxy, $C_1$-$C_4$-alkanoyloxy, amino, $C_1$-$C_4$-alkoxycarbonyl, carbamoyl, phenyl, hydroxyphenyl, methoxyphenyl or by indolyl, and each of the symbols $A^1$, $A^2$ and $A^3$, independently of the others, represents hydrogen, an acyl radical Ac derived from a carboxylic acid, or an above-defined carbamoyl radical of the partial formula II, and salts of such compounds having salt-forming properties.

The invention relates also to processes for the manufacture of the above-mentioned compounds, as well as to pharmaceutical compositions containing those compounds and processes for their manufacture; and also to the therapeutic use of those compounds and pharmaceutical compositions containing them in warm-blooded animals, including humans.

Desferrioxamine B, the basic material of the acylates of the present invention, has already been known for a relatively long time (H. Bickel, H. Keberle and E. Vischer: Helv. Chim. Acta 46, 1385–9 [1963]). Its chemical structure corresponds to the formula

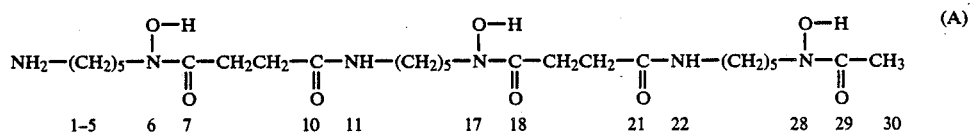

and, in accordance with rule C-06 (replacement nomenclature of the official IUPAC nomenclature), it has the systematic name 6,17,28-trihydroxy-7,10,18,21,29-pentaoxo-6,11,17,22,28-pentaazatriacontylamine. For the sake of simplicity, however, hereinafter the names of the acylates are derived from the trivial names, the position of individual acyl radicals in each case being related to the amino nitrogen N or to the oxygen atoms, designated O, O' and O", of the hydroxy groups in positions 6, 17 and 28, respectively.

One of the most striking properties of desferrioxamine B and its addition salts, which are formed with one equivalent of acid, is the ability to link up, especially with trivalent metal ions, such as chromium(III), aluminium and more especially iron(III) ions, to form stable chelate-like metal complexes. This imparts to desferrioxamine B the valuable pharmacological activity of preventing the deposit of iron-containing pigments in tissue and, where there are existing deposits of iron in the organism, of causing excretion of the iron, for example in the case of haemochromatosis, haemosiderosis, cirrhosis of the liver and poisoning with compounds of trivalent iron. The broad therapeutic use of desferrioxamine B and its salts (for example especially methanesulphonate) therefore extends generally to diseases and pathological conditions of the human body (and of the bodies of other warm-blooded animals) that are associated with excessive loading of the organism with iron(III) ions ($Fe^{+++}$ ions), such as thalassaemia major, sickle cell anaemia, sideroachrestic anaemia, aplastic anaemia and other forms of anaemia in which haemosiderosis (that is to say a local or general increase in iron levels in otherwise undamaged body tissue) is involved. This also includes pathological conditions that develop in patients after repeated blood transfusions or repeated dialysis treatment where the kidney function is impaired or has failed completely. Owing to the complex-forming properties, desferrioxamine B has proved to have a significant activity in the case of diseases caused by iron(III)-dependent microorganisms and parasites, such as, especially, malaria, which is of great importance not only in human medicine but also in veterinary medicine. Also, the formation of complexes with other trivalent metals can be used for the excretion of those metals from the organism, for example for the removal of aluminium in the case of dialysis encephalopathy and osteomalacia, and in the case of Alzheimer's disease.

It has proved a serious disadvantage, however, that desferrioxamine and its salts have only a low and inadequate activity when administered orally, and that a parenteral form of administration is required for all of the possible uses mentioned above. Recommended as an especially effective method, therefore, is, for example, the administration of the active ingredient by means of a slow (8- to 12-hour) subcutaneous infusion which, however, requires either hospitalisation of the patient or, in the case of outpatient treatment, the use of a portable mechanical device, such as an electrically operated infusion syringe. Apart from the fact that they are inconvenient, such solutions involve high treatment costs, which severely restricts their use. In particular, comprehensive treatment of thalassaemia in the countries of the Mediterranean, the Middle East, India and South East Asia, of malaria worldwide and of sickle cell anaemia in African countries is made impossible. These widespread diseases continue to present a serious problem for the health services in these countries and make the search for a simpler and cheaper treatment, preferably by means of an orally active preparation, a priority task in this field.

On theoretical grounds, it may be assumed that the free amino and hydroxy groups of desferrioxamine B provide the essential structural contribution for the chelation of metal ions and thus for the formation of therapeutically applicable metal complexes. If, however, they are blocked by acylation and are therefore, in practice, prevented from participating in complex formation, it is to be expected that, if at all, such N- and/or O,O',O"-acylates and other compounds with blocked amino and/or hydroxy groups will have very limited complex-forming properties and therefore lack the essential prerequisite for therapeutic use.

Contrary to these considerations, it has now been found that, for the same indications in which desferrioxamine B, for example in the form of the established commercial preparation Desferal ®, was hitherto effective only in a parenteral form of administration, the above-characterized novel class of N,N'-disubstituted ureas of the formula I in which $A^1$, $A^2$ and $A^3$ are other than hydrogen have analogous effects when administered orally.

Those compounds of the formula I in which $A^1$, $A^2$ and $A^3$ represent hydrogen are especially effective parenterally. They are, however, intermediates for the manufacture of those compounds of the formula I in which $A^1$, $A^2$ and $A^3$ are other than hydrogen. When administered orally to warm-blooded animals, including humans, at a dosage of approximately from 4 to 40 $\mu$mol/kg, the last-mentioned compounds surprisingly bring about a significant increase in the excretion of metals, such as, especially, iron, relative to known comparative compounds. The daily dose of active ingredient administered to a warm-blooded animal of approximately 70 kg body weight is from approximately 0.5 g to approximately 5 g, for example 2 g.

The present invention relates especially to the N'-(alkoxycarbonylalkyl)-ureas derived from desferrioxamine B and defined at the beginning by formula I.

In the compounds of the formula I according to the invention, the symbols $A^1$, $A^2$ and $A^3$ may differ in meaning from one another also within one and the same category. For example, each of these symbols may represent a different acyl radical Ac and/or a different carbamoyl radical (II). Preferably, however, the 3 symbols all have the same meaning and represent especially an acyl radical Ac or a carbamoyl radical of the formula (II) that preferably has the same meaning as B.

The N-substituted carbamoyl radical (II) is characterized more closely as follows:

$C_1$-$C_4$-alkyl $R_a^1$ is preferably linear, and is, especially, methyl or ethyl. $C_2$-$C_4$-alkenyl $R_a^1$ is especially allyl.

$C_1$-$C_7$-alkylene Alk is preferably $C_1$-$C_4$-alkylene and may, if desired, be branched, its two free valencies originating from two different carbon atoms or from the same carbon atom; it may also carry at any carbon atom one of the substituents mentioned at the beginning. Linear alkylene radicals that have the free valencies at the two terminal carbon atoms, such as tri- to heptamethylene and, especially, ethylene, are preferred. They may also carry, preferably at their terminal carbon atoms, a substituent such as, especially, carbamoyl or $C_1$-$C_4$-alkoxycarbonyl (especially methoxy- or ethoxycarbonyl) or a primary amino group; the first two substituents mentioned are linked preferably to the N-terminal end of the alkylene radical (that is to say to the end that is bonded to the adjacent amino group), and the last substituent mentioned is located preferably at the C-terminal end, that is to say at the end that is bonded to the subsequent carbonyl group. Also preferred are linear alkylene radicals or alkylene radicals branched not more than once, the two free valencies of which originate from the same carbon atom, preferably a terminal carbon atom, that is to say, 1,1-alkylidene radicals such as, especially, methylene, but also ethylidene, 1,1-propylidene etc. These may also carry, preferably at the terminal carbon atom, one of the substituents mentioned at the beginning, such as, for example, a free amino group (especially in 4-amino-1,1-butylidene or 5-amino-1,1-pentylidene), carbamoyl or $C_1$-$C_4$-alkoxycarbonyl, such as one of the above-mentioned $C_1$-$C_4$-alkoxycarbonyl radicals [especially in 2-carbamoyl-1,1-ethylidene, 2-(methoxy- or ethoxy-)-carbonyl-1,1-ethylidene or corresponding 3-substituted 1,1-propylidene radicals, or also a hydroxy or $C_1$-$C_4$-alkanoyloxy (especially acetoxy) group, which is preferably in the 2-position (especially in 2-hydroxy-1,1-ethylidene and 2-hydroxy-1,1-propylidene and corresponding acylated, especially acetylated, radicals). The cyclic substituents are positioned preferably at the methylene group or also in the 2-position of the ethylidene radical.

An especially preferred alkylene radical is one that together with the adjacent amino and carbonyl group is indicated by the partial formula —NH—Alk—CO— or by the symbol —AAA— and that corresponds on the one hand to the general definition of the radical Alk and on the other hand to the structure of certain common naturally occurring $\alpha$-amino acids (in the form of their individual optical isomers or mixtures thereof, especially racemic mixtures). According to general convention, such a "common $\alpha$-amino acid" is one of the 20 amino acids that occur naturally normally as elementary building blocks of peptides and proteins; in accordance with international convention they are usually indicated by an abbreviation consisting of three letters. In the present case, because of the limitation imposed by the general definition of the radical Alk, for example the following acids from this group are not included in the definition according to the invention of the symbol AAA: arginine (Arg), cysteine (Cys), histidine (His) and methionine (Met). The above-mentioned radical —NH—Alk—CO— may thus be, for example, the bivalent radical of one of the following amino acids: glycine (Gly), alanine (Ala), valine (Val), leucine (Leu), isoleucine (Ile), phenylalanine (Pbe), serine (Ser), threonine (Thr), tryptophan (Trp), tyrosine (Tyr), asparagine (Asn), glutamine (Gln) and lysine (Lys). Corresponding especially preferred radicals of the partial formula II are accordingly represented by the partial formula —CO—AAA—O—$R_a^1$(IIA) in which $R_a^1$ has the above-mentioned general and preferably means and —AAA— represents a radical of a specific common $\alpha$-amino acid which is limited by the above general definition of Alk and is in the form of an individual optical isomer or a mixture thereof. A preferred optically individual form is the "natural" isomer of the L-series, and there are preferred as isomeric mixtures those in which the two antipodes are present in equal amounts, that is to say racemates.

—AAA— represents especially the glycine radical (—Gly—) and the whole radical of formula II is especially —CO—Gly—O—$R_a^1$ (IIB) in which $R_a^1$ is especially methyl or ethyl.

Preferably, Alk represents ethylene, that is to say —AAA— is the bivalent radical of $\beta$-alanine.

The acyl radical Ac is derived from hydrocarbylcarboxylic acids or from monoesters of carbonic acid and corresponds to the formula Z—C(=O)— in which Z represents either hydrogen (and thus forms the formyl radical), or hydrocarbyl $R^o$ (and thus forms the radical of an unsubstituted or substituted acyclic, carbocyclic, carbocyclicacyclic, heterocyclic or heterocyclic-acyclic monocarboxylic acid), or represents di-lower alkylamino (and thus represents the acyl radical of N-di-lower alkylcarbamic acid), or is alternatively hydrocarbyloxy $R^o$—O— (and represents the acyl radical of a monoesterified carbonic acid).

The hydrocarbyl radical (hydrocarbon radical) $R^o$ is an acyclic (aliphatic), carbocyclic or carbocyclic-acyclic hydrocarbon radical that in total has preferably a maximum of 40, especially a maximum of 20, and more especially a maximum of 9, carbon atoms and may be saturated or unsaturated, unsubstituted or substituted. Instead of one, two or more carbon atoms it may alternatively contain identical or different hetero atoms such as, especially, oxygen, sulphur and nitrogen, in the acyclic and/or cyclic moiety; in the latter case it is called a heterocyclic radical (heterocyclyl radical) or a heterocyclic-acyclic radical.

Unsaturated radicals are those that contain one or more multiple bonds (double and/or triple bonds). Cyclic radicals in which at least one 6-membered carbocyclic or 5- to 8-membered heterocyclic ring contains the maximum number of non-cumulated double bonds are referred to as aromatic. Carbocyclic radicals in which at least one ring is in the form of a 6-membered aromatic ring (that is to say a benzene ring) are referred to as aryl radicals.

Unless indicated otherwise, in the present disclosure organic radicals designated "lower" contain a maximum of 7, preferably a maximum of 4, carbon atoms.

An acyclic hydrocarbon radical is especially an alkyl, alkenyl, alkadienyl or alkynyl radical that is branched or, preferably, linear.

A carbocyclic hydrocarbon radical is especially a mono-, bi- or poly-cyclic cycloalkyl, cycloalkenyl or cycloalkadienyl radical, or a corresponding aryl radical containing aromatic rings, preferably one having a maximum of 12 ring carbon atoms and containing from 5- to 7-membered, especially 6-membered, rings. Carbocyclic-acyclic radicals are those in which an acyclic radical, especially one having a maximum of 7, preferably a maximum of 4, carbon atoms, such as especially methyl, ethyl or vinyl, carries one or more carbocyclic, optionally aromatic radicals of the above definition.

An aryl radical is especially a phenyl radical, or also a naphthyl radical such as 1- or 2-naphthyl, a biphenylyl radical such as, especially, 4-biphenylyl, and also an anthryl, fluorenyl or azulenyl radical, or an analogue thereof with one or more saturated rings. Preferred aryl-lower alkyl and -lower alkenyl radicals are, for example, phenyl-lower alkyl or phenyl-lower alkenyl having a terminal phenyl radical, such as, for example, benzyl and phenethyl, and styryl and cinnamyl, respectively, and also o-, m- and p-tolyl. Heterocyclic radicals, including heterocyclic-acyclic radicals, are especially monocyclic, or alternatively bi- or poly-cyclic, aza, thia, oxa, thiaza, oxaza, diaza, triaza or tetraza radicals of aromatic character, as well as corresponding partially or, especially, fully saturated heterocyclic radicals of this type; such radicals may optionally, for example like the above-mentioned carbocyclic or aryl radicals, carry other acyclic, carbocyclic or heterocyclic radicals and/-or may be mono-, di- or poly-substituted by functional groups. The acyclic moiety in heterocyclic-acyclic radicals has, for example, the meaning given for the corresponding carbocyclic-acyclic radicals. If a heterocyclyl radical as a direct substituent $R^o$ in the symbol Z is positioned at the oxygen atom, its free valency must originate from one of its carbon atoms.

As has already been mentioned, a hydrocarbyl radical (including a heterocyclyl radical) $R^o$ may be substituted by one, two or more substituents (functional groups) of identical or different kinds; the following substituents are especially suitable: free, etherified and esterified hydroxy groups; mercapto and lower alkylthio groups and optionally substituted phenylthio groups; halogen atoms such as chlorine and fluorine, but also bromine and iodine; oxo groups that are in the form of formyl (that is to say aldehydo) and keto groups, and also in the form of corresponding acetals and ketals; azido and nitro groups; primary, secondary and, preferably, tertiary amino groups, primary or secondary amino groups protected by conventional protecting groups, acylamino groups and diacylamino groups, and also optionally functionally modified sulpho groups, such as sulphamoyl groups or sulpho groups present in salt form. None of these functional groups may be positioned at the carbon atom from which the free valency to the oxygen atom originates; preferably, they are separated from this free valency (and thus from the hetero atom) by two or more carbon atoms. The hydrocarbyl radical may also carry free and functionally modified carboxy groups, such as carboxy groups present in salt form or esterified carboxy groups; carbamoyl, ureidocarbonyl or guanidinocarbonyl groups optionally carrying one or two hydrocarbon radicals; and cyano groups.

An etherified hydroxy group present as a substituent in the hydrocarbyl radical is, for example, a lower alkoxy group, such as a methoxy, ethoxy or tert.-butoxy group, which may also be substituted by halogen atoms, especially in the 2-position, or by lower alkoxy radicals, especially in the 2-position, such as in the 2-methoxyethoxy radical. An especially preferred arrangement of the etherified hydroxy groups is in oxaalkyl radicals in which a preferably linear alkyl contains, instead of several carbon atoms, oxygen atoms that are preferably separated from one another by several (especially 2) carbon atoms, so that they form an optionally repeating group (—O—CH$_2$CH$_2$—)n in which n=from 1 to 14 or even substantially more.

An esterified hydroxy group present as a substituent in the hydrocarbyl radical carries an acyl radical $Ac^o$ having a maximum of 12 carbon atoms that also, within this total number of carbon atoms, may be substituted analogously to the radical Ac, or is lactonised by a carboxy group also present in the hydrocarbyl radical.

An esterified carboxy group present as a substituent in the hydrocarbyl radical is one in which the hydrogen atom has been replaced by one of the above-characterized hydrocarbon radicals, preferably a lower alkyl or phenyl-lower alkyl radical; examples of an esterified carboxy group are especially methoxy-, ethoxy-, tert.-butoxy- and benzyloxy-carbonyl groups, and also lactonised carboxy groups.

A preferred amino group is one of the formula

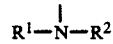

in which each of $R_a{}^1$ and $R_a{}^1$, independently of the other, represents hydrogen, unsubstituted acyclic $C_1$–$C_7$-hydrocarbyl (such as, especially, $C_1$–$C_4$-alkyl or $C_1$–$C_4$-alkenyl) or monocyclic optionally $C_1$–$C_4$-alkyl-, $C_4$–$C_4$-alkoxy-, halo- and/or nitro-substituted aryl, aralkyl or aralkenyl having a maximum of 10 carbon atoms, wherein the carbon-containing radicals may be bonded to one another by a carbon-carbon bond or by an oxygen or sulphur atom or by a nitrogen atom optionally substituted by hydrocarbyl. In such a case they form together with the nitrogen atom of the amino group a nitrogen-containing heterocyclic ring.

A preferred hydrocarbyl radical $R^o$ in the acyl radical $R^o$—C(=O)— is, for example, $C_1$–$C_{19}$-alkyl or $C_2$–$C_{19}$-alkenyl, especially such a radical that has a linear chain when there are more than 5 carbon atoms and that may carry the following substituents: a carboxy group that may optionally also be present in salt form or in the form of a cyano group, a carbamoyl group or a $C_1$–$C_4$-alkyl ester ($C_1$–$C_4$-alkoxycarbonyl group), and that is preferably in the $\omega$-position, an amino group of the above-defined formula

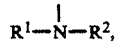

or one or more halogen atoms, especially fluorine or chlorine, which are preferably in the vicinity of the carbonyl group. Another preferred acyl radical of this type is a bicyclic or, especially, monocyclic aroyl radical, especially benzoyl, that may also carry one or more of the following substituents: halogen atoms, especially chlorine or fluorine, nitro groups, $C_1$–$C_4$-alkyl radicals, especially methyl, hydroxy groups and etherified hydroxy groups, especially $C_1$–$C_4$-alkoxy such as methoxy, phenoxy and methylenedioxy, and also carboxy groups that may also be present in salt form or in the form of a cyano group or a $C_1$–$C_4$-alkyl ester ($C_1$–$C_4$-alkoxycarbonyl). Preferably, the aroyl radicals carry no more than 2 such substituents, and especially carry only one. Also preferred are analogous heteroaroyl radicals, especially those that are derived from pyridine, furan, thiophene and imidazole, and from the analogues thereof with a fused benzo ring (such as quinoline, isoquinoline, benzofuran and benzimidazole) and that are optionally also substituted as indicated above. Preferred acyl radicals of this type are also derived from benzyl and styryl (that is to say phenacetyl and cinnamoyl), and may also be substituted in the manner indicated above.

Carboxylic acids forming the basis of the especially preferred acyl radical of the formula $R^o$—C(=O)— are, for example, the following: aliphatic monocarboxylic acids having a maximum of 20 carbon atoms, such as lower alkanecarboxylic acids, for example propionic, butyric, isobutyric, valeric, isovaleric, caproic, trimethylacetic, oenanthic and diethylacetic acid and, especially, acetic acid, as well as lauric, myristic, palmitic and stearic acid and also oleic acid, elaidic acid, linoleic acid and linolenic acid, but also corresponding halogenated lower alkanecarboxylic acids, such as trifluoroacetic acid, chloroacetic acid, bromoacetic acid or o-bromoisovaleric acid, carbocyclic and carbocyclic-acyclic monocarboxylic acids, for example cyclopropane-, cyclopentane- and cyclohexane-carboxylic acid, and cyclopentane- and cyclohexaneacetic acid or -propionic acid, respectively; aromatic carbocyclic carboxylic acids, for example benzoic acid, that may be mono- or poly-substituted in the manner indicated above; aryl- or aryloxy-lower alkanecarboxylic acids and the analogues thereof unsaturated in the chain, for example phenyla-cetic and phenoxyacetic acids, phenylpropionic acids and cinnamic acids each optionally substituted in the manner indicated above for benzoic acid; and heterocyclic acids, for example furan-2-carboxylic acid, 5-tert.-butylfuran-2-carboxylic acid, thiophene-2-carboxylic acid, nicotinic or isonicotinic acid, 4-pyridinepropionic acid, and pyrrole-2- or -3-carboxylic acids optionally substituted by lower alkyl radicals; also corresponding $\alpha$-amino acids, especially the naturally occurring $\alpha$-amino acids of the L-series, for example glycine, phenylglycine, proline, leucine, valine, tyrosine, histidine and asparagine, preferably in an N-protected form, that is to say in a form in which the amino group is substituted by a conventional amino-protecting group, for example one of the above-mentioned amino-protecting groups; and also dicarboxylic acids such as oxalic acid, malonic acid, mono- or di-lower alkylmalonic acids, succinic acid, glutaric acid, adipic acid, erucic acid, maleic acid, a phthalic, quinolinic, isoquinolinic or phenylsuccinic acid optionally substituted by halogen, such as fluorine, chlorine or bromine, and/or by lower alkyl, hydroxy, lower alkoxy and by nitro, as well as, also, glutamic acid and aspartic acid, the last two acids preferably having protected amino groups. As has already been stated, the second carboxy group may be either free or functionally modified, for example in the form of a $C_1$–$C_4$-alkyl ester, an amide or a salt, preferably a physiologically tolerable salt, with a salt-forming basic component. There come into consideration especially metal or ammonium salts, such as alkali metal and alkaline earth metal salts, for example sodium, potassium, magnesium or calcium salts, and ammonium salts with ammonia or suitable organic amines.

An acyl radical Ac derived from monoesters of carbonic acid is characterized by the partial formula $R^o$—O—CO—. Such acyl radicals are, for example, those in which $R^o$ has the following preferred meanings of an acyclic hydrocarbyl radical: $C_1$–$C_{20}$-alkyl, $C_2$–$C_{20}$-hydroxyalkyl in which the hydroxy group is in any position apart from the 1-position, but is preferably in the 2-position, cyano-[$C_1$–$C_{20}$]-alkyl in which the cyano group is preferably in the 1- or $\omega$-position, or carboxy-[$C_1$–$C_{20}$]-alkyl in which the carboxy group is preferably in the 1- or $\omega$-position and may optionally also be in salt form or in the form of a carbamoyl or $C_1$–$C_4$-alkyl ester ($C_1$–$C_4$-alkoxycarbonyl) or benzyl ester (benzyloxycarbonyl), as well as, also, a linear (mono- or di- to hexa-)-oxaalkyl having from 4 to 20 chain members, wherein one or more of the carbon atoms, from C-3 on, of a linear $C_4$–$C_{20}$-alkyl have been replaced by oxygen atoms that are separated from one another by at least 2 carbon atoms and are preferably in positions 3, 6, 9, 12, 15 and 18.

Salts of compounds of the above formula I having salt-forming properties are derived especially from those compounds in which there is a free amino group as substituent in an acyl radical Ac and/or in the radical of the formula II and are acid addition salts, especially pharmaceutically acceptable, non-toxic acid addition salts with inorganic acids, for example hydrochloric acid, hydrobromic acid, sulphuric acid or phosphoric acids, or with organic acids, such as sulphonic acids, such as aromatic sulphonic acids, for example benzenesulphonic acid, p-toluenesulphonic acid or naphthalene-2-sulphonic acid, or especially aliphatic sulphonic acids, for example methanesulphonic acid, ethanesulphonic acid, 2-hydroxyethanesulphonic acid and ethane-1,2- disulphonic acid, and also carboxylic acids, for example acetic acid, propionic acid, glycolic acid, succinic acid, maleic acid, hydroxymaleic acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid.

Owing to the close relationship between the novel compounds in free form and in the form of their salts, including also those acid addition salts that can be used as intermediates, for example in the purification of the novel compounds or for the identification thereof, hereinbefore and hereinafter references to free compounds shall also, where appropriate with regard to context, optionally include the corresponding salts.

The compounds of the present invention have valuable properties, especially pharmacological activities, since they have a physiological action that is similar in basic character to the action of desferrioxamine B. They can therefore be used for the same kind of therapeutic indications as the latter, but with the considerable advantage that they can be administered orally or rectally, for example especially for the treatment of functional disorders in which the concentration of trivalent iron ($Fe^{3+}$ ion) in body cells is abnormally high, such as in the case of haemochromatosis and haemosiderosis. Since, moreover, they also bind aluminium ions in a similar manner, such as, for example, in the case of dialysis encephalopathy, osteomalacia and Alzheimer's disease, they can also be used successfully in those areas of indication.

Preferred are compounds of the formula I in which B represents a carbamoyl radical of the partial formula II in which $R_a^1$ represents $C_1$–$C_4$-alkyl and Alk represents $C_1$–$C_4$-alkylene, and $A^1$, $A^2$ and $A^3$ represent hydrogen, alkanoyl having up to 10 carbon atoms, lower alkoxycarbonyl, 2-(2-methoxyethoxy)-ethoxycarbonyl, di-lower alkylaminocarbonyl or a carbamoyl radical of the partial formula II in which $R_a^1$ represents $C_1$–$C_4$-alkyl and Alk represents $C_1$–$C_4$-alkylene, $A^1$, $A^2$ and $A^3$ all having the same meaning. Among these compounds, attention is drawn especially to those compounds of the formula I in which B represents ethoxycarbonylmethylaminocarbonyl or 2-ethoxycarbonylethylaminocarbonyl and $A^1$, $A^2$ and $A^3$ represent ethoxycarbonylmethylaminocarbonyl, 2-ethoxycarbonylethylaminocarbonyl, hydrogen, n-octanoyl, ethoxycarbonyl, 2-(2-methoxyethoxy)-ethoxycarbonyl or diethylaminocarbonyl, $A^1$, $A^2$ and $A^3$ all having the same meaning, and more especially to those in which $A^1$, $A^2$ and $A^3$ represent ethoxycarbonylmethylaminocarbonyl, 2-ethoxycarbonylethylaminocarbonyl, n-octanoyl, ethoxycarbonyl or 2-(2-methoxyethoxy)ethoxycarbonyl, and to those in which $A^1$, $A^2$ and $A^3$ represent di-lower alkylaminocarbonyl.

Most especially preferred are the compounds of the formula I mentioned in the Examples.

An especially preferred compound according to the invention is N,O,O',O''-tetra-(ethoxycarbonylmethylcarbamoyl)-desferrioxamine B of the formula I in which each of the symbols B, $A^1$, $A^2$ and $A^3$ represents the radical of the formula —CO—Gly—O—$R_a^1$ in which $R_a^1$ is ethyl. Also preferred is the analogous compound in which $R_a^1$ is methyl. When administered orally to rats, the first-mentioned compound has an effect that is comparable to that of parenterally administered desferrioxamine B at the same dosage. Attention is drawn especially also to a compound of the formula I in which B represents the radical of the formula —CO—Gly—O—$R_a^1$ in which $R_a^1$ is ethyl or methyl, and each of the symbols $A^1$, $A^2$ and $A^3$ represents hydrogen or, especially, octanoyl, ethoxycarbonyl or 2-(2-methoxyethoxy)-ethoxycarbonyl.

Most especially preferred are analogous compounds in which the symbol B represents 2-ethoxycarbonylethylaminocarbonyl, and especially N,O,O',O''-tetra-(2-ethoxycarbonylethylaminocarbonyl)desferrioxamine B.

According to the invention, compounds of the formula I are manufactured using conventional analogy processes generally known, for example from peptide chemistry, by (a) reacting a derivative of desferrioxamine B of the formula IV

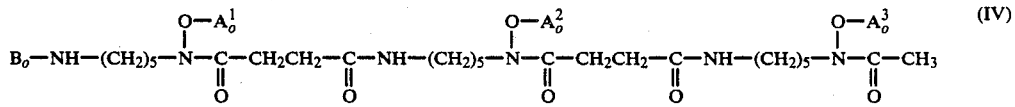

in which $B_o$ represents hydrogen or an organic silyl group Sil and each of the symbols $A_o^1$, $A_o^2$ and $A_o^3$, independently of the others, represents hydrogen, an organic silyl group Sil or an abovedefined acyl radical Ac, with an isocyanatocarboxylic acid ester of the formula III

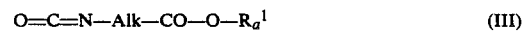

in which Alk and $R_a^1$ have the meanings given above and in which an additional amino-group that may be present in the radical Alk is in protected form, or (b) reacting a derivative of desferrioxamine B of the formula V

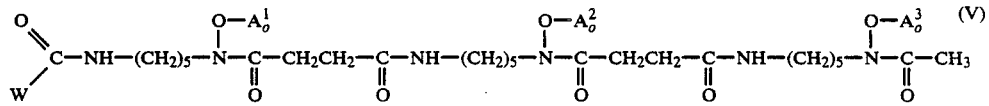

in which W is chlorine or 1-imidazolyl, and in which each of the symbols $A_o^1$, $A_o^2$ and $A_o^3$, independently of the others, represents hydrogen, an organic silyl group Sil or an above-defined acyl radical Ac, with an amino acid ester of the formula VI

in which Alk and $R_a^1$ have the meanings given above and in which an additional amino group that may be present in the radical Alk is in protected form, and, if desired, removing any N- and/or O-silyl groups and/or amino-protecting groups that may be present to free the corresponding hydroxy and amino groups, respectively, and, if desired, acylating a resulting compound of the formula I in which at least one of the symbols $A^1$, $A^2$ and $A^3$ is hydrogen to a compound of the formula I in which the corresponding symbols represent Ac or a carbamoyl radical of the partial formula II and/or, if desired, converting a resulting free compound of the formula I having salt-forming properties into a salt and/or freeing a compound of the formula I from such a salt.

The reaction in accordance with the invention of the starting material of the formula IV according to process variant (a) with an isocyanatocarboxylic acid ester of the formula III or with a derivative thereof protected at the additional amino group that may be present is carried out in a manner known per se using conventional general methods, the reaction being so controlled, by suitable selection of the reaction conditions, that all of the free hydroxy groups present in the starting material IV, and also the free or silylated terminal amino group, are substituted. Under customary reaction conditions the silylamino group is acylated by the carbamoyl group (II), whereas the O-silyl groups prevent O-acylation. For this purpose it is possible to use, for example, an excess of isocyanatocarboxylic acid ester of the formula III undiluted or, alternatively, dissolved in a minimum amount of an inert solvent, such as a chlorinated hydrocarbon (for example chloroform or dichloromethane). If desferrioxamine B is employed as starting material, it is usually used in the form of an acid addition salt, especially in the form of a hydrochloride or methanesulphonate, from which the base is freed in situ in the reaction mixture using an aprotic organic base. The reaction is carried out with the strict exclusion of water and of protic solvents (such as, especially, lower alkanols). The reaction temperature is usually from approximately 0° to approximately 80° C., especially in the region of room temperature or slightly above. The reaction is carried out under basic conditions and is accelerated by catalysis especially with strong organic bases such as, especially, 1,8-diazabicyclo[5.4.0]undec-7-ene and similar cyclic bases, or 4-dialkylaminopyridines, for example 4-dimethylamino- or 4-diethylamino-pyridine. There are suitable for freeing the desferrioxamine B from the salt form (and as additional solvent) excess aprotic organic bases such as tertiary amines, for example triethylamine, ethyldiisopropylamine, tributylamine, N,N-dimethyl- and N,N-diethyl-aniline, N-methyl- and N-ethylpiperidine or -morpholine and N,N'-dimethylpiperazine, and also nitrogen-containing heteroaromatic bases such as pyridine, collidine and quinoline.

Usually, the reaction is carried out in solution or suspension in inert aprotic organic solvents or appropriate mixtures thereof, such as cyclic ethers (for example dioxan or tetrahydrofuran), tertiary amides (for example N,N-dimethylformamide, N,N-dimethylacetamide, N-methylpyrrolidone and hexamethylphosphorus triamide), dimethyl sulphoxide, and also tertiary amines (for example those mentioned above) or acetonitrile or similar lower alkyl cyanides. The reaction is preferably rarried out with intensive stirring in order to provide better mixing of components that are sparingly soluble or sparingly miscible with one another.

Compounds of the formula I in which B has a meaning other than $A^1$, $A^2$ and $A^3$ may advantageously be manufactured starting from a compound of the formula IV in which $B_o$ and at least one (but preferably all) of the symbols $A_o^1$, $A_o^2$ and $A_o^3$ represents an organic silyl group (Sil) of the formula

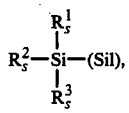

in which each of $R_s^1$ and $R_s^2$, independently of the other, represents unsubstituted $C_1$–$C_8$-hydrocarbyl and $R_a^1$ represents unsubstituted $C_1$–$C_8$-hydrocarbyl or chlorine.

The hydrocarbyl radicals $R_s^1$ and $R_s^2$ present in the organic silyl group Sil are especially $C_1$–$C_8$-alkyl radicals, for example hexyl, 4-methylpentyl, pentyl, ethyl and, especially, methyl, and also aryl and aralkyl radicals, for example phenyl or p-tolyl and benzyl or phenethyl, respectively; preferably, the two radicals are the same. The symbol $R_s^3$ may represent chlorine or have one of the meanings mentioned for the symbols $R_s^1$ and $R_s^2$, all three symbols preferably having the same meaning; $R_s^3$ represents especially methyl.

A suitable organic silyl group Sil is, for example, trimethylsilyl, tribenzoylsilyl, phenyl-dimethylsilyl, benzyl-dimethylsilyl, hexyldimethylsilyl, tert.-butyl-dimethylsilyl, triethylsilyl, diethylchlorosilyl and, especially, dimethyl-chlorosilyl and, more especially, trimethylsilyl.

The reaction of such an (N- and O-)-silylated starting material with the reagent of the formula III is also preferably carried out under the general conditions described above, only the N-silylated amino group being selectively substituted by the radical (II) whilst the O-bonded silyl groups remain and are removed in the subsequent solvolysis together with the N-silyl group (freeing the hydroxy groups and the acylamino group). The solvolysis may be carried out in conventional manner with a protic reagent (including water), which may simultaneously act as solvent, and preferably with acid catalysis. Advantageously, after the main reaction a lower alkanol, such as ethanol or, especially, methanol, (and, where appropriate, a strong acid, such as hydrogen chloride) is added to the reaction mixture, by means of which the removed silyl groups are converted to readily volatile lower aliphatic silyl ethers that can be removed by distillation.

The above-described silylated starting materials of the formula IV can, especially, be formed in situ directly in the reaction medium by reacting desferrioxamine B or an acid addition salt thereof (or a partially O-acylated analogue), in the presence of an aprotic organic base such as one of those mentioned above, especially pyridine, (which can simultaneously act as solvent), with a silylation reagent, especially a silyl halide of the formula Sil-Hal in which Sil has the meaning given above and Hal represents bromine or, especially, chlorine. An especially preferred silylation reagent is, for example, a tri-lower alkylsilyl chloride such as trimethylsilyl chloride, or alternatively a di-lower alkyldichlorosilane such as dimethyldichlorosilane. Preferably, the silylation agent is added in excess; its presence does not disturb or impair the main reaction (the reaction with an isocyanate of the formula III) in any way, but rather it removes any possible trace of moisture, which bas a detrimental effect. Therefore, the main reaction can be carried out after the silylation and in the same reaction medium and can even be combined with the subsequent solvolytic removal of the silyl groups, so that all 3 steps (manufacture of the starting material, treatment with isocyanate and removal of the silyl groups) can be carried out in one and the same reaction medium. The excess silylation reagent and also the excess isocyanate are advantageously destroyed and converted into volatile products under the conditions of the solvolysis; in the course of this the silyl halides yield hydrogen chloride, which advantageously catalyses the solvolysis.

Variant (b) of the process according to the invention is also carried out in a general manner that is known per se, it being possible for the reaction of the N-chloroformyl or N-(1-imidazolyl-carbonyl) derivative of desferrioxamine B with an amino acid ester of the formula VI to be carried out under analogous conditions and in the same solvents as process variant (a). In the amino acid ester VI, an additional amino group that may be present must be in protected form, and preferably also carboxy groups may be in ester form. The compound may also be used in the form of an acid addition salt, in which case the reactive free form of the amino group is formed in situ by the action of the organic base, such as pyridine, used as reaction medium. The starting materials of the formula IV in which $B_o$ represents chloroformyl or the 1-imidazolylcarbonyl group and each of $A_o^1$, $A_o^2$ and $A_o^3$, independently of the others, represents hydrogen, the silyl group Sil or the acyl radical Ac, may be manufactured in a general manner known per se, for example by the abovedescribed process. Thus, for example, desferrioxamine B or an acid addition salt thereof (or a partially O-acylated analogue may be treated in the presence of an aprotic organic base (such as one of those described above) with a silylation reagent (such as one of those mentioned above) and the resulting (N- and O-)-silylated derivative may be reacted with phosgene and bis-(1-imidazolyl)-carbonyl, respectively, preferably with a molar equivalent thereof. The two reactions are in general carried out one after the other in the same medium. The resulting N-chloroformyl or N-(1-imidazolylcarbonyl) derivative, respectively, can either be subjected to careful solvolytic removal of the silyl groups and isolated in individual form (if desired, after acylation, in the form of an O-acylate), or alternatively reacted, still in silylated form, with the amino acid ester VI, with the silyl groups being removed only after that. All steps are carried out under the above-described general conditions, preferably in pyridine or a similar heterocyclic base that acts both as solvent and as the basic reagent.

Suitable protecting groups for the temporary protection during the reaction according to the invention of an amino group that may be present are customary amino-protecting groups that are used in the synthesis of the peptide chain and, together with corresponding methods for their removal, are described in detail in syroptical reviews and reference works such as Houben-Weyl: Methoden der organischen Chemie; 4th edition, vol 15/I and II, E. Wünsch (editor): Synthese von Peptiden (Georg-Thieme Verlag, Stuttgart; 1974). It is preferable to use amino-protecting groups that can be removed by acidolysis or under neutral conditions.

Suitable amino-protecting groups are, for example, trityl substituted by methyl, methoxy, halogens and/or by nitro, or preferably the unsubstituted trityl (triphenylmethyl) group, which can be removed by solvolysis (acidolysis) under very mild conditions, such as with only approximately 50% acetic acid. Also, phenylsulphenyl groups substituted in the ring, especially the 2-nitrophenylsulphenyl group $o$-$O_2N$—$C_6H_4$—$S$—, should be mentioned; the latter can be removed, for example, by an acid-catalysed solvolysis or acidolysis, e.g. already by means of pyridine hydrochloride.

The most important amino-protecting groups are, however, esterified oxycarbonyl radicals of the partial formula $R^o$—O—CO— in which $R^o$ is a hydrocarbyl radical that can be removed under neutral conditions and/or by acidolysis.

Such amino-protecting groups are, for example, benzyloxycarbonyl groups optionally substituted in the aromatic ring by halogen atoms, nitro groups, lower alkyl groups or by lower alkoxy groups, such as unsubstituted benzyloxycarbonyl (i.e. carbobenzoxy), p-bromo- or p-chloro-benzyloxycarbonyl, p-nitrobenzyloxycarbonyl, p-methoxybenzyloxycarbonyl and p-tolyloxycarbonyl, and furfuryloxycarbonyl, as well as, also, 2-(4-biphenylyl)-2-propoxycarbonyl, and similar aralkoxycarbonyl radicals described in Swiss Patent No. 509 266. These radicals can, as described in detail hereinafter, be removed under neutral conditions by hydrogenolysis or, preferably, acidolysis.

Another such acyl radical $R^o$—O—CO— is, for example, especially tert.-butoxycarbonyl, or also an analogous radical such as isopropoxycarbonyl, tert.-amyloxycarbonyl (that is 1,1-dimethylpropoxycarbonyl), diisopropylmethoxycarbonyl, cyclopentyloxycarbonyl, cyclohexyloxycarbonyl, d-isobornyloxycarbonyl and adamantyloxycarbonyl. These radicals can be removed especially under acidic conditions (acidolysis) as described in detail hereinafter.

Yet another acyl radical $R^o$—O—CO— is, for example, a $\beta$-(trihydrocarbylsilyl)-ethoxycarbonyl radical, such as $\beta$-(tri-lower alkylsilyl)-ethoxycarbonyl, for example especially $\beta$-(trimethylsilyl)ethoxycarbonyl. Such radicals form together with the amino group to be protected corresponding $\beta$-trihydrocarbylsilylethoxycarbonylamino groups (for example the D-trimethylsilylethoxycarbonylamino group) which, although resistant under conditions of acidic hydrolysis and hydrogenolysis, can be removed under quite specific very mild conditions by the action of fluoride ions.

Attention is drawn especially also to allyloxycarbonyl which can be removed not only by acidolysis but, especially, also under very mild neutral conditions with dimedone, or by the specific reducing action of tributyltin hydride catalysed with palladium-(O)-tetrakis-(triphenylphosphine) complex.

The subsequent removal of the amino-protecting group in accordance with the invention is carried out in a generally known manner, specific conditions for the individual types of structure being described in detail in the relevant literature (see, for example, Houben-Weyl, loc. cit.). The acidolysis (including acidic hydrolysis) is effected, for example, with trifluoroacetic acid, hydrogen fluoride, hydrogen bromide and hydrogen chloride, optionally in the presence of water, such as with hydrochloric acid, and, in the case of acid-sensitive protecting groups, also with a lower aliphatic carboxylic acid, such as formic acid and/or acetic acid, optionally in the presence of water. The groups that can be removed under neutral conditions, especially those that contain benzyl radicals, are preferably removed by hydrogenolysis, for example by palladium-catalysed hydrogenation. The $\beta$-silylethoxycarbonyl groups are preferably removed with fluoride-ion-yielding agents, for example with fluorides of quaternary organic bases, such as tetraethylammonium fluoride or tetrabutylammonium fluoride, in neutral organic solvents.

Depending on the method of operation, end products with unsubstituted amino groups are obtained in the form of bases or acid addition salts. The bases can be obtained in a manner known per se from the acid addition salts. In turn, it is possible by reacting the bases with acids, for example with those that form the above-mentioned salts, to obtain acid addition salts that can be used therapeutically.

If desired, in resulting end products of the formula I in which at least one (and preferably all) of the symbols $A^1$, $A^2$ and $A^3$ represents hydrogen, the corresponding free hydroxy groups can be acylated by treating such a compound with an agent that introduces the acyl radical Ac or a carbamoyl radical of the formula II.

The agent used for introducing an acyl radical Ac is an acylation agent generally customary for this purpose; there are used especially acylation agents of the formula AcY in which Ac has the above-indicated general and preferred meanings and Y represents a reactive functionally modified hydroxy group or an additional single bond to the radical Ac, the other end of which replaces a hydrogen atom in the radical Ac.

A suitable agent introducing the carbamoyl radical of the formula II is, for example, a carbonylamino acid ester of the formula III defined above, with which the acylation is carried out under the above-mentioned general conditions. An acylation agent derived from the above-defined acyl radical Ac is especially one in which Y is an esterified hydroxy group, for example one that is esterified with a strong inorganic acid, such as a hydrohalic acid (for example hydrochloric, hydrobromic or hydriodic acid), a pseudohydrohalic acid such as azoimide or imidazole (with removal of the hydrogen atom from the 1-N-atom), an oxygen-containing mineral acid, such as phosphoric acid and, especially, sulphuric acid, or a strong organic, such as aliphatic or aromatic, sulphonic acid (for example methane and ethane-sulphonic acid or benzene-, p-toluene-, p-nitrobenzene- and p-chlorobenzene-sulphonic acid). Such an esterified group then forms a mixed anhydride with the acyl radical. Attention is drawn especially to mixed anhydrides with hydrohalic acids and pseudohydrohalic acids, such as acid bromides, acid chlorides, acid azides and 1-imidazolyl derivatives of the formula $R^o$—CO—Hal and $R^o$—O—CO—Hal, respectively, in which Hal represents bromine or azido and preferably chlorine or 1-imidazolyl and $R^o$ has the meanings given above. Suitable reagents of this type that are of importance especially in the manufacture of starting materials for process variant (b) are phosgene and its less toxic bis-(1-imidazolyl)carbonyl analogue (and similar reagents). They are as a rule used in equimolar amounts so that the second reactive group Y is retained in the product and can be modified subsequently.

An example of an acylation agent AcY for introducing a di-lower alkylaminocarbonyl radical, for example the diethylaminocarbonyl radical, is di-lower alkylcarbamoyl chloride, for example diethylcarbamoyl chloride.

The reactive esterified hydroxy group can, however, also be esterified either by the radical of another carboxylic acid, especially a stronger carboxylic acid such as formic acid, chloroacetic acid or, especially, trifluoroacetic acid, and form the basis of a mixed anhydride, or, alternatively, by the same acyl radical and form a symmetrical carboxylic acid anhydride of the formula Ac¹—O—Ac¹, especially of the formula $R^o$—CO—O—CO—$R^o$ or $R^o$—O—CO—O—CO—O—$R^o$.

Acylation agents of the formula AcY in which Y represents an additional bond to the radical Ac are derived especially from acyl radicals of carboxylic acids that carry a hydrogen atom at the carbon atom that is adjacent to the carboxy group; they belong to the category of ketenes of the formula $R_a^o$=C=O in which $R_a^o$ represents hydrocarbylidene, that is to say a bivalent radical of aliphatic character corresponding to the radical $R^o$ and in which the functionalised carbon atom is bonded by single bonds to adjacent carbon and/or hydrogen atoms.

The reaction with the acylation agent of the formula AcY is carried out under known process conditions that are generally customary in organic chemistry for the acylation of hydroxy compounds, usually at temperatures of from the freezing point to the boiling point of the reaction mixture, such as in a temperature range of from approximately $-10°$ to approximately $+160°$, especially from approximately $20°$ to approximately $+50°$, at atmospheric pressure or elevated pressure, in heterogeneous phase (such as a suspension) while stirring or shaking or, especially, in homogeneous liquid phase, such as in an excess of liquid reagent or, especially, in the presence of solvents, especially organic solvents, and where appropriate in the presence of acid-binding inorganic or organic agents. Suitable solvents are, for example, aprotic organic solvents of low polarity, such as halogenated, especially chlorinated, aliphatic hydrocarbons such as chloroform and dichloromethane, and especially polar aprotic solvents such as aliphatic and cyclic ethers, for example diethyl ether, 1,2-dimethoxyethane and diisopropyl ether, and dioxan and tetrahydrofuran, respectively, lower aliphatic esters and amides such as ethyl acetate and formamide, acetamide, N,N-dimethylacetamide and dimethylformamide respectively, and also acetonitrile, dimethyl sulphoxide and hexamethylphosphorus triamide; the solvents may also be used in suitable combinations, for example to increase the solubility of components.

The acid-binding agents used may in principle be any basic compounds such as, on the one hand, organic nitrogen-containing bases, for example tertiary amines of the triethylamine, ethyldiisopropylamine, N,N-dimethylaniline, N-ethylpiperidine or N,N'-dimethylpiperazine type, or aromatic heterocyclic bases of the pyridine, collidine, quinoline or 4-dimethylaminopyridine type, and, on the other hand, inorganic compounds having a basic reaction, such as alkali metal hydroxides, carbonates and hydrogen carbonates, and also salts of carboxylic acids, such as sodium or potassium acetate. Finally, this function can also be performed by nitrogen-containing compounds having a neutral reaction, which at the same time are often also advantageous solvents, for example carboxylic acid amides, especially lower aliphatic carboxylic acid amides, such as those mentioned above, and cyclic amides such as N-methylpyrrolidone, and also amido derivatives of carbonic acid such as urethanes and urea. Conversely, the above-mentioned bases, especially those of the pyridine type, can act as solvents.

If the hydrocarbyl radical $R^o$ is substituted by functional groups that might also react during the acylation, such as free carboxy, hydroxy and, especially, amino groups, these groups are normally temporarily protected, or are preferably already in a protected form in the acylation agent used, and are freed of these protecting groups when acylation is complete.

Esterification, for example, is one of the most usual methods of protecting carboxy groups. An esterified carboxy group is in general freed by conventional hydrolysis, especially by the action of bases (such as, especially, alkali metal hydroxides, carbonates or hydrogen carbonates) or, alternatively, in the case of suitable esters such as those of tertiary alcohols (for example tert.-butylalcohol), by acidolysis, for example by means of hydrogen fluoride or trifluoroacetic acid. Esters with benzylalcohols can also be removed by conventional hydrogenolysis.

The groups to be used for the temporary protection of hydroxy groups and methods for their removal are also generally known, for example from the synthesis of peptides. Hydroxy groups are protected especially in the form of esters with carboxylic acids, such as with lower alkanoic acids, or with monoesters of carbonic acid (for example formates or acetates on the one hand or tert.-butoxy- or benzyloxy-carbonates on the other hand), or alternatively in the form of ethers such as, especially, those of tertiary alcohols (for example tert.-butylalcohol), or also in the form of acetals (for example especially in the form of 2-tetrahydropyranyl ether). The former protecting groups are customarily removed analogously to esterified carboxy groups; the latter two protecting groups are removed especially by acidolysis.

The protecting groups that can be used for the temporary protection of primary and secondary amino groups correspond to those discussed in detail above in the main process.

The most important starting materials, especially desferrioxamine B and its acid addition salts on the one hand, or the N-carbonylamino acid esters, especially those derived from common α-amino acids, on the other hand, are known or are obvious. Those that are not known, such as some of the isocyanatoalkanoic acid esters (carbonylamino acid esters) that are to be used for the acylation, can be obtained in a conventional manner known per se, for example by treating an amino acid ester, in the form of an acid addition salt and optionally with the protection of an amino group that is present as a substituent and is not to be reacted, with at least one equivalent, and preferably an excess amount, of phosgene, optionally in the presence of a non-acylatable amine (such as one of those mentioned above). Resulting compounds having a protected amino group are advantageously used as such in the main reaction and the protecting group is not removed until afterwards.

The starting materials used in the process according to the present invention are preferably those that result in the compounds described at the beginning as being especially valuable.

The invention relates also to those embodiments of the process in which a starting material is formed under the reaction conditions or is used in the form of a derivative, for example a salt.

The present invention relates also to pharmaceutical compositions that contain as active ingredient one of the novel pharmacologically active compounds of the formula I, especially one of those given special mention hereinbefore for this use. Especially preferred are preparations and compositions for enteral, such as especially oral, administration. The preparations contain the active ingredient on its own or, preferably, together with a pharmaceutically acceptable carrier. The dosage of the active ingredient depends on the disease to be treated and on the species, age, weight and individual condition, and also on the mode of administration, but in general it corresponds in quantity approximately to that of parenterally administered desferrioxamine B or a salt thereof.

The pharmaceutical compositions contain preferably from approximately 5% to approximately 95% of the active ingredient, single dose forms of administration preferably containing from approximately 20% to approximately 90%, and non-single dose forms of administration preferably containing from approximately 5% to approximately 20%, of active ingredient; pharmaceutical preparations in dosage unit form, such as dragées, tablets or capsules and suppositories, contain from approximately 0.1 g to approximately 3.0 g, preferably from approximately 0.3 g to approximately 1.0 g, of the active ingredient.

The pharmaceutical compositions of the present invention are manufactured in a manner known per se. for example by means of conventional mixing, granulating, confectioning, dissolving or lyophilising processes. For example, pharmaceutical compositions for oral use can be obtained by combining the active ingredient with one or more solid carriers, if desired granulating a resulting mixture, and processing the mixture or granulate, if desired and/or appropriate after the addition of additional adjuncts, to form tablets or dragée cores.

Suitable carriers are especially fillers such as sugars, for example lactose, saccharose, mannitol or sorbitol, cellulose preparations and/or calcium phosphates, for example tricalcium phosphate or calcium hydrogen phosphate, and also binders such as starches, for example corn, wheat, rice or potato starch, methylcellulose, hydroxypropylmethylcellulose, sodium carboxymethylcellulose and/or polyvinylpyrrolidone and/or, if desired, disintegrators such as the above-mentioned starches, also carboxymethyl starch, crosslinked polyvinylpyrrolidone, or alginic acid or a salt thereof such as sodium alginate. Additional adjuncts are especially flow-regulating agents and lubricants, for example silica, talc, stearic acid or salts thereof, such as magnesium or calcium stearate, and/or polyethylene glycol.

Dragée cores are provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations such as acetylcellulose phthalate or hydroxypropylmethylcellulose phthalate. Colouring substances or pigments may be added to the tablets or dragée coatings, for example for the purposes of identification or to indicate different doses of active ingredient.

Other orally administrable pharmaceutical compositions are dry-fill capsules made of gelatin, and also soft, sealed capsules made of gelatin and a plasticiser such as glycerine or sorbitol. The dry-filled capsules may contain the active ingredient in the form of a granulate, for example in a mixture with fillers such as corn starch, binders and/or glidants such as talc or magnesium stearate, and optionally stabilisers. In soft capsules the active ingredient is preferably dissolved or suspended in suitable liquids such as fatty oils, paraffin oil or liquid polyethylene glycols, it being possible also for stabilisers to be added.

Other forms of oral administration are, for example, syrups prepared in customary manner that contain the active ingredient in, for example, suspended form and in a concentration of approximately from 5% to 20%, preferably approximately 10%, or in a similar concentration that produces, for example when dispensing 5 or 10 ml, a suitable single dose. Also suitable are, for example, pulverulent or liquid concentrates for preparing shakes, for example in milk. Such concentrates can also be packed in single-dose quantities.

The invention relates also to a method of treating diseases in which, as has been described hereinbefore, an excess of iron(III) or aluminium is present in the body, characterized in that a prophylactically or therapeutically effective amount of a compound of the formula I is administered, preferably perorally. There are used for this especially the above-mentioned pharmaceutical compositions, a daily dose of from approximately 0.5 g to approximately 15 g, preferably from approximately 1.5 g to approximately 7.5 g, of a compound of the present invention being administered to a warm-blooded animal of approximately 70 kg body weight.

The following Examples illustrate the present invention; temperatures are in degrees Celsius.

EXAMPLE 1

N,O,O',O''-tetra-(ethoxycarbonylmethylcarbamoyl)-desferrioxamine B

With the strict exclusion of moisture, 14 ml (0.1 mol) of triethylamine, a solution of 13 g (0.1 mol) of isocyanatoacetic acid ethyl ester (ethyl-N-carbonylglycinate) in 100 ml of dichloromethane, and 50 mg of 4-dimethylaminopyridine (as catalyst) are added in succession, at room temperature, to an intensively stirred suspension of 6.56 g (0.01 mol) of desferrioxamine β-methanesulphonate in 200 ml of acetonitrile, 200 ml of dichloromethane and 20 ml of dimethylsulphoxide and the whole is stirred at room temperature until all the solid material has dissolved (from 3 to 4 hours). After an additional hour, the reaction mixture is freed of volatile components in vacuo, and the weakly acidic residue (pH approximately 5) is taken up in 300 ml of water, adjusted to a pH of 7.7 with 1N sodium hydroxide and extracted three times with 500 ml of dichloromethane each time. The combined organic extracts are washed several times with water, dried over sodium sulphate and freed of solvent in vacuo. The solid amorphous residue is the crude title compound of a usable purity. For further purification it can be chromatographed on silica gel with mixtures of dichloromethane/tetrahydrofuran/2-propanol in a ratio of approximately from 85:15:0 to 80:15:5. In a molecular weight determination using mass spectroscopy the foam-like practically colourless product exhibits a value MH+ of 1078, which agrees with the value 1077.153 calculated for the formula $C_{45}H_{76}N_{10}O_{20}$; Rf=0.24 (dichloromethane:2-propanol=85:15), Rf=0.31 (dichloromethane:methanol=90:10), Rf=0.59 (dichloromethane:methanol 85:15), 360 MHz-$^1$H-NMR, DMSO-$d_6$, 40° C.: δ=1.19 and 1.26 and 1.38 and 1.51 (m; 30 H), 1.93 (s; 3 H), 2.30 (t; 4 H), 2.48 (t; 4 H), 3.00 (m; 6 H), 3.54 (t; 6 H), 3.74 (d; 2 H), 3.82 (d; 6 H), 4.11 (m; 8 H), 6.02 (broad; 2 H), 7.63 (broad; 3 H), 8.23 (broad; 2 H).

An equivalent amount (5.97 g) of desferrioxamine B-hydrochloride can be converted in an analogous manner to the identical end product.

EXAMPLE 2

N-(ethoxycarbonylmethylcarbamoyl)-desferrioxamine B 50.0 ml (400 mmol) of trimethylchlorosilane (TMS) are added over a period of 10 minutes to a suspension of 26.3 g (40 mmol) of desferrioxamine B-methanesulphonate in 300 ml of pyridine and the whole is stirred at room temperature for 3 hours. 9.3 g (72 mmol) of isocyanatoacetic acid ethyl ester are added to the reaction solution at 22° over a period of 10 minutes and the whole is stirred at room temperature for a further 6 hours. By adding 150 ml of methanol excess reagents are destroyed and the silyl groups are removed, and solvents are removed by distillation. The solid residue is dried under a high vacuum and crystallised first from water and then from methanol/dichloromethane; m.p. 177°–178°.

EXAMPLE 3

N-(ethoxycarbonylmethylcarbamoyl)-O,O',O''-trioctanoyldesferrioxamine B of the formula I in which
B=C$_2$H$_5$O—CO—CH$_2$—NH—CO— and
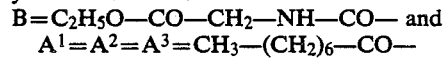

In the course of 5 minutes 5.65 ml (33 mmol) of octanoyl chloride are added to a suspension of 6.9 g (10 mmol) of N-(ethoxycarbonylmethylcarbamoyl) desferrioxamine B (from Example 2) in 120 ml of pyridine at 23° under argon. The reaction solution is stirred for 5 hours at room temperature, the excess acylation agent is destroyed by the addition of 100 ml of methanol, and the volatile components are removed by distillation. The residue is taken up in 350 ml of phosphate buffer of pH 7.4 and extracted with dichloromethane. After drying, the dichloromethane solution is chromatographed twice on silica gel; elution with mixtures of dichloromethane/isopropyl alcohol (v/v ratio of 97:3 to 94:6) yields the product in the form of a colourless oil that solidifies to crystals at room temperature. The elemental analysis of the product corresponds to the theoretical analysis for the title compound $C_{54}H_{97}N_7O_{14}$ (1068.4); m.p. 65° C.

EXAMPLE 4

N-(ethoxycarbonylmethylcarbamoyl)-O,O',O''-tri-[2-(2-methoxyethoxy)-ethoxycarbonyl]-desferrioxamine B of the formula I in which
B=C$_2$H$_5$O—CO—CH$_2$—NH—CO— and
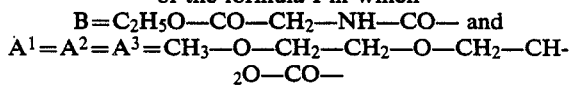

In the course of 5 minutes a solution of 7.86 g (43 mmol) of 2-(2-methoxyethoxy)-ethylchloroformic acid ester in 40 ml of toluene is added dropwise to a suspension of 6.9 g (10 mmol) of N-(ethoxy-carbonylmethylcarbamoyl)-desferrioxamine B (from Example 2) in 120 ml of pyridine under argon at 23°. The reaction mixture is stirred at room temperature for 17 hours, the excess acylation agent is destroyed by the addition of 160 ml of methanol, and the volatile components are removed by distillation. The residue is taken up in 350 ml of phosphate buffer of pH 7.4 and extracted with dichloromethane. After drying, the dichloromethane solution is evaporated to dryness, dissolved in a minimum amount of heptane/dichloromethane (1:2) and chromatographed on silica gel; elution with mixtures of dichloromethane/isopropylalcohol (v/v ratio of from 94:6 to 90:10) yields the product in the form of a yellowish oil. The elemental analysis of the product corresponds to the theoretical analysis for the title compound $C_{48}H_{85}N_7O_{23}$ (1128.2); retention time in the high pressure liquid chromatogram 4.6 minutes (starting material: 2.4 minutes) under the following conditions:

Column: Hypersil-ODS-5 μm (4.0×120 mm), linear gradient from solution A, consisting of 2.5 millimolar phosphate buffer pH 3.0, and solution B, consisting of 20% by volume of 2.5 millimolar phosphate buffer pH 3.0 and 80% by volume of acetonitrile, at a flow rate of 2.3 ml/minute.

EXAMPLE 5

N-(ethoxycarbonylmethylcarbamoyl)-O,O',O''-tri-(ethoxycarbonyl)-desferrioxamine B of the formula I in which $B=C_2H_5O—CO—CH_2—NH—CO—$ and $A^1=A^2=A^3=CH_3—CH_2—O—CO—$ In a manner analogous to that described in Example 4, but using 40 mmol of ethylchloroformic acid ester as acylation agent, the title compound is obtained in the form of a colourless oil that on elemental analysis gives correct values for $C_{39}H_{67}N_7O_{17}$ (906.0); Rf=0.40 (chloroform:acetone=70:30), Rf=0.55 (dichloromethane:2-propanol=90:10), Rf=0.90 (dichloromethane:methanol=80:20).

EXAMPLE 6

N,O,O',O''-tetra-(2-ethoxycarbonylethylaminocarbonyl)desferrioxamine B 1.13 g (2 mmol) of desferrioxamine B-methanesulphonate are placed in 25.0 ml of pyridine. 2.40 ml (17 mmol) of triethylamine and then 25.6 ml (9.6 mmol) of 3-isocyanatopropionic acid ethyl ester in toluene are added dropwise to the suspension, and the reaction mixture is stirred at room temperature. After 4 hours, a further 10.7 ml (4 mmol) of 3-isocyanatopropionic acid ethyl ester in toluene is added dropwise thereto. After 25 hours, the excess reagent is rendered inactive by the addition of methanol. The reaction mixture is filtered and concentrated to dryness. The crude product is taken up in dichloromethane and chromatographsd on silica gel several times. The product is obtained in the form of a yellowish oil using dichloromethane/methanol (97:3 to 94:6). The honey-like product slowly crystallises. The resulting title compound has the following characteristic data: m.p. 55°-60° C., Rf=0.15 (dichloromethane:2-propanol=90:10), Rf=0.39 (dichloromethane:methanol=90:10).

The starting material is obtained as follows:

Stage 6.1: 15.36 g (100 mmol) of β-alanine ethyl ester are taken up in 600 ml of toluene and heated to 90° C. The educt does not dissolve until warmed. 63 ml (120 mmol) of a 20% phosgene/toluene solution are added thereto over a period of 10 minutes at from 90° to 95° C. under an argon atmosphere. The reaction mixture is stirred at 90° C. After 2 hours the majority of the educt has reacted. The isocyanate is produced quantitatively by stirring the reaction mixture overnight at approximately 90° C.

The reagent solution, containing 3-isocyanatopropionic acid ethyl ester, is cooled and used further.

EXAMPLE 7

N-(2-ethoxycarbonylethylaminocarbonyl)-desferrioxamine B 1.13 g (2 mmol) of desferrioxamine B-methanesulphonate are placed in 40.0 ml of pyridine. 0.34 ml (2.4 mmol) of triethylamine and then 3.03 ml (24 mmol) of trimethylchlorosilane are added to the suspension, HCl formation being observed. After 15 minutes, 6.40 ml (2.4 mmol) of 3-isocyanatopropionic acid ethyl ester in toluene (see stage 6.1) are added dropwise to the silylated educt over a period of 3 minutes, and the reaction mixture is stirred at room temperature. There are added in portions thereto, over a period of 29 hours, a further 0.34 ml (2.4 mmol) of triethylamine, 0.60 ml (4.8 mmol) of trimethylchlorosilane and 12.8 ml (4.8 mmol) of 3-isocyanatopropionic acid ethyl ester in toluene. After 48 hours, the excess reagent is rendered inactive by the addition of methanol and the reaction mixture is concentrated to dryness. The residue is taken up in water, the title product being precipitated in the form of crystals. It is recrystallised from dichloromethane. M.p. 170°-171° C.

EXAMPLE 8

N-(2-ethoxycarbonylethylaminocarbonyl)-desferrioxamine B 38 g (33 mmol) of N,O,O',O''-tetra-(2-ethoxycarbonylethylaminocarbonyl)-desferrioxamine B (see Example 6) are dissolved in 4000 ml of acetonitrile/phosphate buffer pH 8 (v/v=1:2) and hydrolysed at from 30° to 37° C. Over a period of several days the proportion of tetra-substituted starting material shifts by way of tri- and disubstituted intermediates to the desired N-mono-substituted title compound. The crude product is crystallised from water and recrystallised from dichloromethane. The properties of the resulting product are the same as those of the end product of Example 7.

EXAMPLE 9

N-(ethoxycarbonylmethylaminocarbonyl)-desferrioxamine B 2.63 g (2.45 mmol) of N,O,O',O''-tetrakis-(ethoxycarbonylmethylcarbamoyl)-desferrioxamine B are dissolved in 340 ml of acetonitrile/phosphate buffer pH 8 (v/v=1:2) and hydrolysed at 30° C. Over a period of several days the proportion of tetrasubstituted starting material shifts by way of tri- and di-substituted intermediates to the desired N-monosubstituted title product. The crude product is crystallised from water and recrystallised from methanol/dichloromethane. The properties of the resulting title product are the same as those of the product obtained according to Example 2.

EXAMPLE 10

N-(2-ethoxycarbonylethylaminocarbonyl)-O,O',O''-tri-octanoyl-desferrioxamine B

Starting N-(2-ethoxycarbonylethylaminocarbonyl)-desferrioxamine B, the title compound is obtained in amorphous form analogously to Example 3 after chromatography on silica gel (dichloromethane:2-propanol=97:3 to 90:10, v/v).

EXAMPLE 11

N-(2-ethoxycarbonylethylaminocarbonyl)-O,O',O"-tri-[2-(2-methoxyethoxy)-ethoxycarbonyl]-desferrioxamine B The title compound is obtained analogously to Example 4 starting from N-(2-ethoxycarbonylethylaminocarbonyl)-desferrioxamine B.

EXAMPLE 12

N-(2-ethoxycarbonylethylaminocarbonyl)-O,O',O"-triethoxycarbonyl-desferrioxamine B The title compound is obtained analogously to Example 5 starting from N-(2-ethoxycarbonylethylaminocarbonyl)-desferrioxamine B.

EXAMPLE 13

N-(ethoxycarbonylmethylaminocarbonyl)-O,O',O"-tri-(diethylaminocarbonyl)-desferrioxamine B 100 ml of pyridine are added to 5.52 g (8 mmol) of N-ethoxycarbonylmethyl-desferrioxamine B. 4.47 ml (32 mmol) of triethylamine and then 4.56 ml (36 mmol) of diethylcarbamoyl chloride are added dropwise to the light suspension at 23° C. under an argon atmosphere. The reaction mixture is stirred overnight at room temperature. After 16 hours the solution is clear and dark-orange. The excess reagent is rendered inactive by the addition of 100 ml of methanol. The solvent is removed. The solid residue is taken up in 350 ml of water and extracted with dichloromethane.

The crude product is dissolved in dichloromethane and chromatographed on silica gel. The title product is obtained in the form of a yellowish oil using dichloromethane/2-propanol (97:3 to 90:10); Rf=0.29 (dichloromethane:2-propanol=90:10), Rf=0.42 (dichloromethane:methanol=90:10).

EXAMPLE 14

Manufacture of 1000 capsules with 260 mg of active ingredient [for example N,O,O',O"-tetra-(ethoxycarbonylmethylcarbamoyl)-desferrioxamine B or one of the end products of Examples 3 to 6 and 10 to 13] per capsule

| Composition | |
|---|---|
| active ingredient | 260 g |
| talc | 36 g |
| wheat starch | 24 g |
| magnesium stearate | 16 g |
| lactose | 4 g |
| | 340 g |

Preparation

The pulverulent substances are forced through a sieve having a mesh width of 0.6 mm and thoroughly mixed. Gelatin capsules are each prepared with 340 mg of this mixture using a capsule-filling machine.

EXAMPLE 15

Preparation of 1000 capsules containing 105 mg of active ingredient [for example N,O,O',O"-tetra-(ethoxycarbonylmethylcarbamoyl)-desferrioxamine B or one of the end products of Examples 3 to 6 and 10 to 13] per capsule

| Composition | |
|---|---|
| active ingredient | 105 g |
| ethylcellulose | 3 g |
| stearic acid | 3 g |
| | 111 g |

Preparation

The ethylcellulose and the stearic acid are dissolved in 120 ml of methylene chloride, the active ingredient is added and the composition is pushed through a sieve having a mesh width of 0.6 mm at a temperature of approximately 40°, the methylene chloride evaporating. 111 mg of the resulting granulate are introduced into 0.5 ml gelatin capsules using a capsule-filling machine.

EXAMPLE 16

N-(2-ethoxycarbonylethylaminocarbonyl)-O,O',O"-tri(ethoxycarbonylmethylaminocarbonyl)-desferrioxamine B N-(2-ethoxycarbonylethylaminocarbonyl)-desferrioxamine B is placed in pyridine (dried with KOH). 3.3 equivalents of isocyanatoacetic acid ethyl ester are added dropwise to the suspension over a period of 5 minutes at room temperature under an argon atmosphere. The reaction mixture is stirred at room temperature. After 1 hour, a further 2.7 equivalents of reagent is added.

After 23 hours, 200 ml of methanol are added to the reaction solution. After stirring for 30 minutes the solvent is distilled off. The solid residue (dried under a high vacuum) is taken up in 400 ml of 1M phosphate buffer pH 7.4 and extracted twice with 350 ml of dichloromethane. The organic phases are filtered through silicone paper, concentrated and dried under a high vacuum. Chromatography on silica gel (dichloromethane/2-propanol 94:6 to 90:10) yields the title compound.

EXAMPLE 17

N-(2-ethoxycarbonylethylaminocarbonyl)-O,O',O"-tri(diethylaminocarbonyl)-desferrioxamine B The title compound is obtained analogously to Example 13 starting from N-(2-ethoxycarbonylethylaminocarbonyl)-desferrioxamine B.

I claim:

1. A compound of the formula I $$B-NH-(CH_2)_5-\underset{\underset{O}{\|}}{N}-\underset{\underset{O}{\|}}{\overset{\overset{O-A^1}{|}}{C}}-CH_2CH_2-\underset{\underset{O}{\|}}{C}-NH-(CH_2)_5-$$

$$-\underset{\underset{O}{\|}}{\overset{\overset{O-A^2}{|}}{N}}-C-CH_2CH_2-\underset{\underset{O}{\|}}{C}-NH-(CH_2)_5-\underset{\underset{O}{\|}}{\overset{\overset{O-A^3}{|}}{N}}-C-CH$$

in which B represents a carbamoyl radical of the partial formula $-CO-NH-Alk-CO-O-R_a^1$ (II) in which $R_a^1$ represents $C_1-C_4$-alkyl or $C_2-C_4$-alkenyl and Alk represents $C_1-C_7$-alkylene that is unsubstituted or substituted by hydroxy, $C_1-C_4$-alkanoyloxy, amino, $C_1-C_4$-alkoxycarbonyl, carbamoyl, phenyl, hydroxyphenyl, methoxyphenyl or by indolyl, and each of the symbols $A^1$, $A^2$ and $A^3$, independently of the others, represents hydrogen, an above-defined carbamoyl radical of the partial formula II, or an acyl radical Ac
  (a) of the formula Z—C(=O)—, in which Z represents
    (aa) hydrogen,
    (ab) alkyl or alkenyl having up to 19 carbon atoms each of which is unsubstituted or substituted by carboxy, cyano, carbamoyl, ($C_1$-$C_4$)-alkoxycarbonyl, amino or halogen,
    (ac) phenyl which is unsubstituted or substituted by one or two substituents selected from halogen, nitro, $C_1$-$C_4$-alkyl, hydroxy, $C_1$-$C_4$-alkoxy, phenoxy, methylenedioxy, carboxy, cyano and $C_1$-$C_4$-alkoxycarbonyl,
    (ad) pyridyl, furyl, theinyl, imidazolyl, quinolyl, isoquinolyl, benzofuryl, benzimidazolyl,
    (ae) benzyl or styryl, or
    (af) di-lower alkylamino; or
  (b) of the formula $R^o$—O—CO wherein $R^o$ represents
    (ba) $C_1$-$C_{20}$-alkyl which is unsubstituted or substituted by cyano, carboxy, carbamoyl, ($C_1$-$C_4$)-alkoxycarbonyl or benzyloxycarbonyl,
    (bb) $C_2$-$C_{20}$-hydroxyalkyl in which the hydroxy group is in any position apart from the 1-position, or
    (bc) linear (mono- or di- to hexa-)-oxaalkyl having from 4 to 20 chain members, wherein one or more of the carbon atoms, from C-3 on, of a linear $C_4$-$C_{20}$-alkyl have been replaced by oxygen atoms that are separated from one another by at least 2 carbon atoms;
or a salt of such a compound having salt-forming properties.

2. A compound according to claim 1 in which each of $A^1$, $A^2$ and $A^3$ represents the same acyl radical Ac or carbamoyl radical of the partial formula II.

3. A compound according to claim 1 in which $A^1$, $A^2$ and $A^3$ have the same meaning and B represents a radical of the partial formula II wherein $R_a^1$ represents a linear $C_1$-$C_4$-alkyl radical and alk represents a linear $C_1$-$C_7$-alkylene radical, the free valencies of which originate from the two terminal carbon atoms.

4. A compound according to claim 1 in which $A^1$, $A^2$ and $A^3$ have the same meaning and B represents a radical of the partial formula II wherein $R_a^1$ represents a linear $C_1$-$C_4$-alkyl radical and Alk represents a linear 1,1-alkylidene radical or a 1,1-alkylidene radical branched once.

5. A compound of formula I according to claim 1 in which $A^1$, $A^2$ and $A^3$ have the same meaning and B represents a linear $C_1$-$C_4$-alkyl radical and —NH—ALK—CO— represents a bivalent radical of one of the amino acids selected from the group consisting of glycine, alanine, valine, leucine, isoleucine, phenylalanine, serine, threonine, tryptophan, tyrosine, asparagine, glutamine and lysine.

6. A compound according to claim 1 in which $A^1$, $A^2$ and $A^3$ have the same meaning and B represents a radical of the partial formula II wherein $R_a^1$ represents a linear $C_1$-$C_4$-alkyl and Alk represents methylene.

7. A trivalent metal scavenger pharmaceutical composition comprising a trivalent metal scavenging effective amount of a compound of formula I according to claim 1 or a pharmaceutically acceptable salt thereof so as to increase excretion of metals from a warm-blooded animal to which it is administered and a pharmaceutical carrier material.

8. A compound according to claim 1 in which $A^1$, $A^2$ and $A^3$ have the same meaning.

9. A compound according to claim 1 in which each of $A^1$, $A^2$ and $A^3$ represents hydrogen.

10. A compound according to claim 2 of the formula I in which each of the symbols $A^1$, $A^2$, $A^3$ and B represents a radical of the partial formula —CO—NH—Alk—CO—O—$R_a^1$ (II) in which $R_a^1$ represents $C_1$-$C_4$-alkyl and Alk represents $C_1$-$C_7$-alkylene that is unsubstituted or substituted by hydroxy, $C_1$-$C_4$-alkanoyloxy, amino, $C_1$-$C_4$-alkoxycarbonyl, carbamoyl, phenyl, hydroxyphenyl, methoxyphenyl or by indolyl, or a salt of such a compound having salt-forming properties.

11. A compound according to claim 1 in which B represents a carbamoyl radical of the partial formula II in which $R_a^1$ represents $C_1$-$C_4$-alkyl and Alk represents $C_1$-$C_4$-alkylene and each of $A^1$, $A^2$ and $A^3$ represents hydrogen, alkanoyl having up to 10 carbon atoms, lower alkoxycarbonyl, 2-(2-methoxyethoxy)-ethoxycarbonyl, di-lower alkylaminocarbonyl or a carbamoyl radical of the partial formula II in which $R_a^1$ represents $C_1$-$C_4$-alkyl and Alk represents $C_1$-$C_4$-alkylene, $A^1$, $A^2$ and $A^3$ all having the same meaning.

12. A compound according to claim 1 in which B represents ethoxycarbonycarbonylmethylaminocarbonyl or 2-ethoxycarbonylethylaminocarbonyl and each of $A^1$, $A^2$ and $A^3$ represents ethoxycarbonylmethylaminocarbonyl, 2-ethoxycarbonylethylaminocarbonyl, hydrogen, n-octanoyl, ethoxycarbonyl, 2-(2-methoxyethoxy)-ethoxycarbonyl or diethylaminocarbonyl, $A^1$, $A^2$ and $A^3$ all having the same meaning.

13. A compound according to claim 3 in which each of $A^1$, $A^2$ and $A^3$ represents ethoxycarbonylmethylaminocarbonyl, 2-ethoxycarbonylethylaminocarbonyl, n-octanoyl, ethoxycarbonyl or 2-(2-methoxyethoxy)-ethoxycarbonyl.

14. A compound according to claim 3 in which each of $A^1$, $A^2$ and $A^3$ represents di-lower alkylaminocarbonyl.

15. N,O,O',O''-tetra-(ethoxycarbonylmethylcarbamoyl)-desferrioxamine B according to claim 1.

16. N-(ethoxycarbonylmethylcarbamoyl)-desferrioxamine B according to claim 1.

17. N-(ethoxycarbonylmethylcarbamoyl)-O,O',O''-tri-octanoyl-desferrioxamine B according to claim 1.

18. N-(ethoxycarbonylmethylcarbamoyl)-O,O',O''-triethoxycarbonyldesferrioxamine B according to claim 1.

19. N-(ethoxycarbonylmethylcarbamoyl)-O,O',O''-tri-[2-(2-methoxyethoxy)-ethoxycarbonyl]-desferrioxamine B according to claim 1.

20. N,O,O',O''-tetra-(2-ethoxycarbonylethylaminocarbonyl)-desferrioxamine B according to claim 1.

21. N-(2-ethoxycarbonylethylaminocarbonyl)-desferrioxamine B according to claim 1.

22. N-(ethoxycarbonylmethylaminocarbonyl)-desferrioxamine B according to claim 1.

23. N-(2-ethoxycarbonylethylaminocarbonyl)-O,O',O''-trioctanoyl-desferrioxamine B according to claim 1.

24. N-(2-ethoxycarbonylethylaminocarbonyl)-O,O',O''-tri-[2-(2-methoxyethoxy)-ethoxycarbonyl]-desferrioxamine B according to claim 1.

25. N-(2-ethoxycarbonylethylaminocarbonyl)-O,O',O''-tri-(ethoxycarbonyl)-desferrioxamine B according to claim 1.

26. N-ethoxycarbonylmethylaminocarbonyl-O,O',-O''-tri-(diethylaminocarbonyl)-desferrioxamine B according to claim 1.

27. N-(2-ethoxycarbonylethylaminocarbonyl)-O,O',-O''-tri-(ethoxycarbonylmethylaminocarbonyl)-desferrioxamine B according to claim 1.

28. A pharmaceutical composition according to claim 26 for oral administration.

29. A medicinal method of treating pathological conditions in warm-blooded animals that are associated with an excess of iron(III) or aluminium in the body or are caused by iron(III)-dependent pathogenic organisms, characterized in that a prophylactically or therapeutically effective amount of a compound according to claim 1, alone or in the form of a pharmaceutical composition, is administered to the patient.

* * * * *